(12) United States Patent
Ferber

(10) Patent No.: US 6,774,120 B1
(45) Date of Patent: Aug. 10, 2004

(54) METHODS OF INDUCING REGULATED PANCREATIC HORMONE PRODUCTION IN NON-PANCREATIC ISLET TISSUES

(76) Inventor: Sarah Ferber, Sold Street 52/6, Ramat Hasharon (IL), 47225

(*) Notice: Subject to any disclaimer, the term of this patent is extended or adjusted under 35 U.S.C. 154(b) by 0 days.

(21) Appl. No.: 09/584,216

(22) Filed: May 31, 2000

Related U.S. Application Data

(60) Provisional application No. 60/198,532, filed on Apr. 19, 2000, and provisional application No. 60/137,143, filed on Jun. 1, 1999.

(51) Int. Cl.[7] .................. A61K 31/70; A61K 39/00; C07H 21/02; C07H 21/04; A01N 63/00
(52) U.S. Cl. .................. 514/44; 536/23.1; 536/23.5; 424/93.1; 424/191.1; 424/93.2; 435/235.1
(58) Field of Search .................. 514/44; 536/23.1, 536/23.5; 435/325, 235.1; 530/350; 424/93.1, 191.1

(56) References Cited

U.S. PATENT DOCUMENTS

| | | | |
|---|---|---|---|
| 5,741,673 A | 4/1998 | Montminy et al. | |
| 5,849,989 A | 12/1998 | Edlund | |
| 5,858,973 A | 1/1999 | Habener et al. | |
| 2001/0013134 A1 * | 8/2001 | Sarvetnick et al. | 800/18 |
| 2002/0081725 A1 * | 6/2002 | Tsang et al. | 435/366 |

FOREIGN PATENT DOCUMENTS

WO    WO 95/05463    2/1995

OTHER PUBLICATIONS

Milewski et.al.; Conservation of PDX–1 Structure, Function, and Expression in Zebrafish, 1998, Endocrinology, vol. 139: 1440–1449.*
Offield et.al.; PDX–1 is required for pancreatic outgrowth and differentiation of the rostral duodenum, 1996, Development 122: 983–995.*
Ozcan et.al.; Functional expression and analysis of the pancreatic transcription factor PDX–1 in yeast, 2002, Biochemical and Biophysical Research Communications 295: 724–729.*
Ahlgren et.al.; The morphogenesis of the pancreatic mesenchyme is uncoupled from that of the pancreatic epitheliom in IPF1/PDX1–deficeint mice, 1996, Development 122: 1409–1416.*
Anderson; Human gene therapy, 1998, Nature, vol. 392: 25–30.*
Verma et.al.; Gene therapy– promises, problems and prospects, 1997, Nature, vol. 389: 239–242.*
Marshak et.al.; Purification of the B–cell glucose–sensitive factor that transactivates . . . in normal and transormed islet cells, 1996, Proc. Natl. Acad. Sci., vol. 93: 15057–15062.*
Kajimoto et.al.; Suppression of Transcription Factor PDX–1/IPF1/STF–1 Causes No Decrease in Insulin mRNA in MIN6 Cells, 1997, J. Clin. Imvest, vol. 100:1840–1846.*
Seijeffers et.al.; Increase in PDX–1 Levels Suppressess Insulin Gene Expression in RIN 1046–38 Cells. 1999, Endocrinology, vol. 140: 3311–3317.*
Muzzin, P. et al. (1997). *Mol. Endocrinology 11*: 833–837.
Peers, B. et al. Biosis Online, Accession No.: PREV199598090886 (1994).
Jonsson, J. et al. (1994). *Nature 371*: 606–609.
Ferber, S. et al. (2000). *Nature Medicine 6*: 568–572.
Kahn, A. (2000). *Nature Medicine 6*: 505–506.
International Search Report, issued Jan. 12, 2001.
Stoffel et al., Genomics 28 (1), 125–126 (1995): Genbank Accession No. U35632.
Milewski et al., Endocrinology 139 (3), 1440–1449 (1998); Genbank Accession No. AAC41260.
Miller et al., EMBO J. 13, 1145–1156 (1994); Genbank Accession No. AAA18355.
Milewski et al., Endocrinology 139 (3), 1440–1449 (1998); Genbank Accession No. AF036325.
Marshak et al., Proc. Natl. Acad. Sci. USA 93, 15057–15062 (Dec. 1996).

* cited by examiner

Primary Examiner—Deborah J. Reynolds
Assistant Examiner—Joseph Woitach
(74) Attorney, Agent, or Firm—Mintz,Levin,Cohn,Ferris,Glovsky and Popeo, P.C.; Ivor R. Elrifi, Esq.; Cynthia A. Kozakiewicz, Esq.

(57) ABSTRACT

Disclosed are methods and pharmaceutical compositions for inducing pancreatic hormone production.

17 Claims, 5 Drawing Sheets

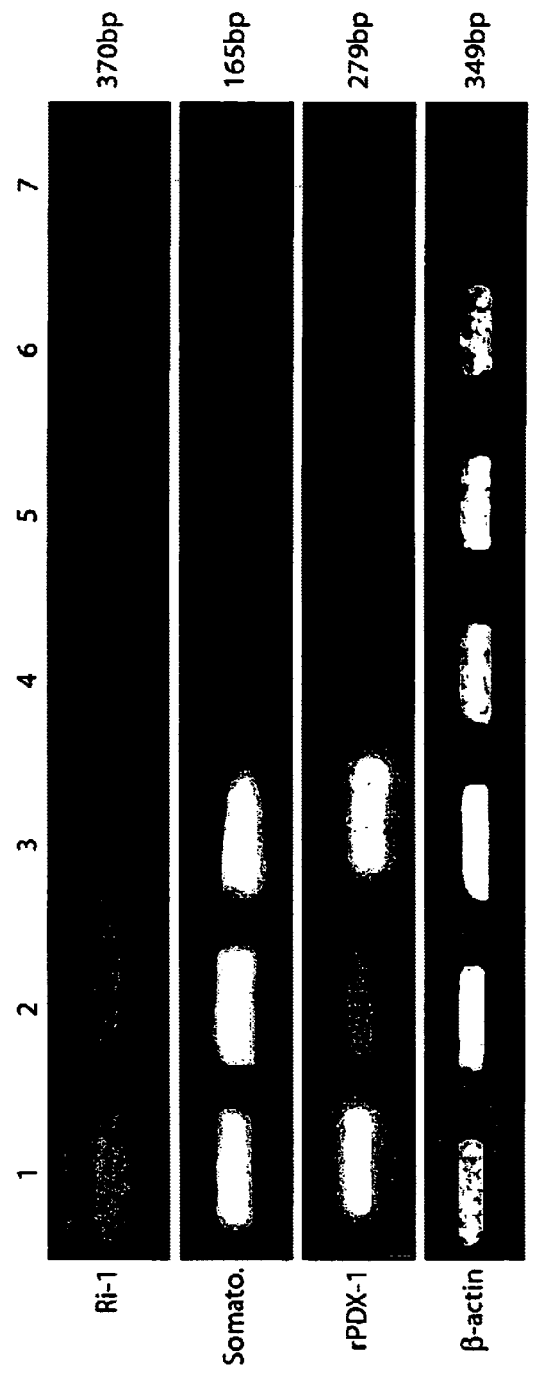
Fig. 6
Fig. 7

SEQUENCE LISTING

```
<160> NUMBER OF SEQ ID NOS: 25

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 1
tccaggtgcc tacaggattc tct                                              23

<210> SEQ ID NO 2
<211> LENGTH: 20
<212> TYPE: DNA
<213> ORGANISM: Artificial Sequence
<220> FEATURE:
<223> OTHER INFORMATION: chemically synthesized

<400> SEQUENCE: 2
ccagtttgca ggctcgctgg                                                  20

<210> SEQ ID NO 3
<211> LENGTH: 20
<212> TYPE: DNA
<213> ORGANISM: Artificial Sequence
<220> FEATURE:
<223> OTHER INFORMATION: chemically synthesized

<400> SEQUENCE: 3
gctgcgtatg cacctcctgc                                                  20

<210> SEQ ID NO 4
<211> LENGTH: 22
<212> TYPE: DNA
<213> ORGANISM: Artificial Sequence
<220> FEATURE:
<223> OTHER INFORMATION: chemically synthesized

<400> SEQUENCE: 4
ctttgtgaac caacacctgt gc                                               22

<210> SEQ ID NO 5
<211> LENGTH: 22
<212> TYPE: DNA
<213> ORGANISM: Artificial Sequence
<220> FEATURE:
```

```
<223> OTHER INFORMATION: chemically synthesized

<400> SEQUENCE: 5
gcagatgctg gtacagcatt gt                                              22

<210> SEQ ID NO 6
<211> LENGTH: 20
<212> TYPE: DNA
<213> ORGANISM: Artificial Sequence
<220> FEATURE:
<223> OTHER INFORMATION: chemically synthesized

<400> SEQUENCE: 6
ttgccctctg ggagcccaaa                                                 20

<210> SEQ ID NO 7
<211> LENGTH: 20
<212> TYPE: DNA
<213> ORGANISM: Artificial Sequence
<220> FEATURE:
<223> OTHER INFORMATION: chemically synthesized

<400> SEQUENCE: 7
cagatgctgg tgcagcactg                                                 20

<210> SEQ ID NO 8
<211> LENGTH: 20
<212> TYPE: DNA
<213> ORGANISM: Artificial Sequence
<220> FEATURE:
<223> OTHER INFORMATION: chemically synthesized

<400> SEQUENCE: 8
tcttcctctg ggagtcccac                                                 20

<210> SEQ ID NO 9
<211> LENGTH: 20
<212> TYPE: DNA
<213> ORGANISM: Artificial Sequence
<220> FEATURE:
<223> OTHER INFORMATION: chemically synthesized

<400> SEQUENCE: 9
cagatgctgg tgcagcactg                                                 20

<210> SEQ ID NO 10
<211> LENGTH: 18
<212> TYPE: DNA
<213> ORGANISM: Artificial Sequence
<220> FEATURE:
<223> OTHER INFORMATION: chemically synthesized

<400> SEQUENCE: 10
atggatgacg atatcgct                                                   18

<210> SEQ ID NO 11
<211> LENGTH: 19
<212> TYPE: DNA
<213> ORGANISM: Artificial Sequence
<220> FEATURE:
<223> OTHER INFORMATION: chemically synthesized

<400> SEQUENCE: 11
atgaggtagt ctgtcaggt                                                  19
```

<210> SEQ ID NO 12
<211> LENGTH: 23
<212> TYPE: DNA
<213> ORGANISM: Artificial Sequence
<220> FEATURE:
<223> OTHER INFORMATION: chemically synthesized

<400> SEQUENCE: 12
ctggttgtct ggacctctga gta                                    23

<210> SEQ ID NO 13
<211> LENGTH: 23
<212> TYPE: DNA
<213> ORGANISM: Artificial Sequence
<220> FEATURE:
<223> OTHER INFORMATION: chemically synthesized

<400> SEQUENCE: 13
ccaacagcag aagtgagtgt gac                                    23

<210> SEQ ID NO 14
<211> LENGTH: 26
<212> TYPE: DNA
<213> ORGANISM: Artificial Sequence
<220> FEATURE:
<223> OTHER INFORMATION: chemically synthesized

<400> SEQUENCE: 14
caagctcgct gggatcactg gagcag                                 26

<210> SEQ ID NO 15
<211> LENGTH: 28
<212> TYPE: DNA
<213> ORGANISM: Artificial Sequence
<220> FEATURE:
<223> OTHER INFORMATION: chemically synthesized

<400> SEQUENCE: 15
gatgtgtctc tcggtcaagt tcaacatc                               28

<210> SEQ ID NO 16
<211> LENGTH: 20
<212> TYPE: DNA
<213> ORGANISM: Artificial Sequence
<220> FEATURE:
<223> OTHER INFORMATION: chemically synthesized

<400> SEQUENCE: 16
cctggctttg ggcggtgtca                                        20

<210> SEQ ID NO 17
<211> LENGTH: 22
<212> TYPE: DNA
<213> ORGANISM: Artificial Sequence
<220> FEATURE:
<223> OTHER INFORMATION: chemically synthesized

<400> SEQUENCE: 17
ctcgggctcc agggcatcat tc                                     22

<210> SEQ ID NO 18
<211> LENGTH: 24
<212> TYPE: DNA
<213> ORGANISM: Artificial Sequence
<220> FEATURE:
<223> OTHER INFORMATION: chemically synthesized -continued

```
<400> SEQUENCE: 18
accagcgact acagcaaata cctc                                          24

<210> SEQ ID NO 19
<211> LENGTH: 21
<212> TYPE: DNA
<213> ORGANISM: Artificial Sequence
<220> FEATURE:
<223> OTHER INFORMATION: chemically synthesized

<400> SEQUENCE: 19
agcaatggcg acttcttctg g                                             21

<210> SEQ ID NO 20
<211> LENGTH: 20
<212> TYPE: DNA
<213> ORGANISM: Artificial Sequence
<220> FEATURE:
<223> OTHER INFORMATION: chemically synthesized

<400> SEQUENCE: 20
gtgaccagct acaatcatag                                               20

<210> SEQ ID NO 21
<211> LENGTH: 20
<212> TYPE: DNA
<213> ORGANISM: Artificial Sequence
<220> FEATURE:
<223> OTHER INFORMATION: chemically synthesized

<400> SEQUENCE: 21
agttctccag ttggtagagg                                               20

<210> SEQ ID NO 22
<211> LENGTH: 20
<212> TYPE: DNA
<213> ORGANISM: Artificial Sequence
<220> FEATURE:
<223> OTHER INFORMATION: chemically synthesized

<400> SEQUENCE: 22
cgtaaagacc tctatgccaa                                               20

<210> SEQ ID NO 23
<211> LENGTH: 20
<212> TYPE: DNA
<213> ORGANISM: Artificial Sequence
<220> FEATURE:
<223> OTHER INFORMATION: chemically synthesized

<400> SEQUENCE: 23
agccatgcca aatgtgtcat                                               20

<210> SEQ ID NO 24
<211> LENGTH: 27
<212> TYPE: DNA
<213> ORGANISM: Artificial Sequence
<220> FEATURE:
<223> OTHER INFORMATION: chemically synthesized

<400> SEQUENCE: 24
gatctgcccc ttgttaataa tctaatg                                       27

<210> SEQ ID NO 25
<211> LENGTH: 27
```

```
-continued
<212> TYPE: DNA
<213> ORGANISM: Artificial Sequence
<220> FEATURE:
<223> OTHER INFORMATION: chemically synthesized
<223> OTHER INFORMATION: chemically synthesized

<400> SEQUENCE: 25
gatccgccct taatgggcca aacggca                                               27
```

METHODS OF INDUCING REGULATED PANCREATIC HORMONE PRODUCTION IN NON-PANCREATIC ISLET TISSUES

RELATED APPLICATIONS

This application claims priority to U.S. Ser. No. 60/137,143 filed Jun. 1, 1999 and U.S. Ser. No. 60/198,532 filed Apr. 19, 2000. The contents of these applications are incorporated herein by reference in their entireties.

FIELD OF THE INVENTION

This invention relates generally to methods of inducing a pancreatic endocrine phenotype and function including pancreatic hormone production in a non-endocrine tissue and in particular to methods and pharmaceutical compositions for treating endocrine related disorders.

BACKGROUND OF THE INVENTION

The endocrine pancreas consists primarily of islet cells that synthesize and secrete the peptide hormone glucagon, insulin, somatostatin and pancreatic polypeptide. Insulin gene expression is restricted to pancreatic islet 6-cells of the mammalian pancreas through control pus mechanisms mediated in part by specific transcription factors. In other cells the insulin, other pancreatic hormones and specific peptidases genes are trancriptionally silent. The homeodomain protein PDX-1 (Pancreatic and Duodenal Homeobox gene-1, also known-as IDX-1, IPF-1, STF-1 or IUF-1) plays a central role in regulating pancreatic islet development and function. PDX-1 is either directly or indirectly involved in islet-cell-specific expression of various genes such as for example insulin, glucagon somatostatin, proinsulin convertase 1/3 (PC 1/3), GLUT-2 and glucokinase. Additionally, PDX-1 mediates insulin gene transcription in response to glucose.

SUMMARY OF THE INVENTION

The invention is based in part on the discovery that ectopic expression of pancreatic and duodenal homobox gene 1 (PDX-1) in liver induces the expression of the silent pancreatic hormone genes and the processing machinery, which converts the prohormones into mature biologically active hormones.

The invention provides methods of inducing pancreatic hormone, e.g., insulin, glucagon and somatostatin levels in a subject. In one aspect, the method includes administering to a subject in need thereof a compound which increases PDX expression or activity in an amount sufficient to induce pancreatic hormone production in the subject. In another aspect, the method includes providing a cell capable of expressing a pancreatic hormone, contacting the cell with a compound which increases PDX expression or activity and introducing the cell into a subject, thereby inducing pancreatic hormone production in the subject. Also provided in the invention is a method of treating a pancreatic-related disorder, e.g., diabetes in a subject. The method includes administering to a subject a therapeutically effective amount of a compound which increases PDX expression.

In another aspect the invention provides a method of inducing a pancreatic islet gene expression profile in a subject. The method includes administering to a subject in need thereof a compound which increases PDX expression or activity in an amount sufficient to induce pancreatic islet gene expression.

In yet a further aspect of the invention is a method inducing or enhancing a pancreatic islet cell phenotype in a cell. The method includes contacting a cell with compound which increases PDX expression or activity in an amount sufficient to induce or enhance pancreatic islet cell phenotype in said cell.

Also included are pharmaceutical composition that includes a compound which increases PDX expression and a pharmaceutically acceptable carrier.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Figure 1:
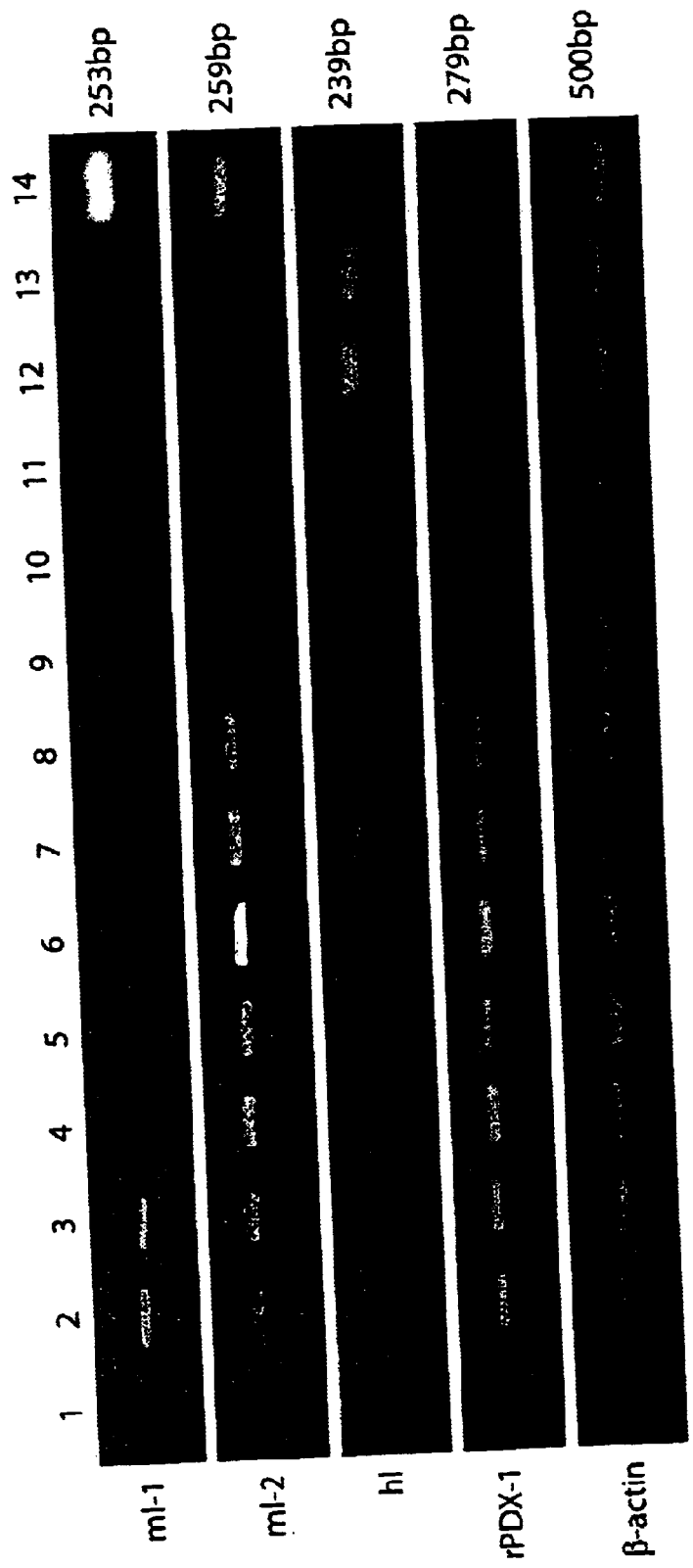
FIG. 1 is an illustration demonstrating detection of mRNA in Balb/c mice liver tissue for mouse insulin I (mI-1), mouse insulin II (mI-2), human insulin, PDX-1 and β-actin after adenovirus treatment as determined by RT-PCR. Lane 1: no DNA (negative control for PCR); lanes 2–6: livers from AdCMV-PDX-1 treated mice lanes 7, 8: livers from AdCMV-PDX-1+AdRIP-1-hIns-treated mice; lanes 9–11: livers from control AdCMV-β-gal+AdRIP-1-hIns-treated mice; lanes 12, 13: livers from AdCMV-hIns-treated mice; lane 14: normal mouse pancreas.

Lane 1: cells treated by AdCMV PDX-1+AdRIP hIns, lane 2: AdCMVβ-galactosidase+AdRIP hIns, lane 3: Control.

FIG. 6 is an illustration demonstrating the induction of Insulin 1 and Somatostatin gene expression in primary monolayer cultures of fetal Fisher rat (E14) hepatocytes. Fetal hepatocytes were isolated from Fisher 344 rat embryos at day 14 of gestation, and plated on collagen covered tissue culture dishes. Cells were infected by AdCMVPDX-1 at 2–5 MOI (multipiplicity of infection=number of viral particles per cell). Total RNA was extracted from the culture 4 days after viral treatment and was analyzed for somatostatin gene expression by RT-PCR. RNA was reversed transcribed as in FIG. 1 using oligo $(dT)_{15}$ primers and amplification by PCR was in performed using primers and conditions as elaborated in Table 1. Lanes 1–3: samples from cells treated by PDX-1, lanes 4–6: untreated samples (control) lane 7: no DNA, PCR products were resolved on 1.7% agarose gel electrophoresis.

FIG. 7 is an illustration demonstrating the Effect of GLUT2 and GK overexpression on the glucose regulation of PDX-1 binding to A3/A4 site on the insulin promoter. RIN-38 cells of intermediate passage were studied untreated (lane 1), treated with AdCMV-GLUT2 or AdCMV-GK (lanes 3,4), or with control AdCMVCAT (lane 5). 48 hours after viral treatments, nuclear extracts were prepared and EMSA analysis was performed using the A3/A4 sequences as probes. Last two lanes: 1 µl of anti-PDX-1 antibody (a gift from C. Wright) was added to the nuclear extract (+) and blocked complex formation. Pre-immune serum was added to the nuclear extract (−) used to identify that PDX-1 is indeed the protein bound to the given portion of the insulin promoter.

DETAILED DESCRIPTION OF THE INVENTION

The invention is based in part on the discovery that ectopic expression of pancreatic and duodenal homobox gene 1 (PDX-1) in liver induces a pancreatic islet cell phenotype in liver cells and results in the expression, production and processing of pancreatic hormones. PDX-1 is also known as IDX-1, IPF-1, STF-1 and IUF-1, all of which are collectively referred to herein as "PDX". Additionally, the invention provides methods and pharmaceutical compositions for treating pancreatic disorders.

In its various aspects and embodiments, the a invention includes administering to a subject or contacting a cell with a compound that increases PDX expression or activity. The compound can be, e.g., (i) a PDX polypeptide; (ii) a nucleic acid encoding a PDX polypeptide; (iii) a nucleic acid that increases expression of a nucleic acid that encodes a PDX polypeptide and, and derivatives, fragments, analogs and homologs thereof. A nucleic acid that increase expression of a nucleic acid that encodes a PDX polypeptide includes, e.g., promoters, enhancers. The nucleic acid can be either endogenous or exogenous.

As used herein, the term "nucleic acid" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded. Preferably, the nucleic acid is a DNA. A nucleic acid that increase expression of a nucleic acid that encodes a PDX polypeptide includes, e.g., promoters, enhancers. The nucleic acid can be either endogenous or exogenous.

Suitable sources of nucleic acids encoding PDX include for example the human PDX nucleic acid (and the encoded protein sequences) available as GenBank Accession Nos. U35632 and AAA88820, respectively. Other sources include rat PDX nucleic acid and protein sequences are shown in GenBank Accession No. U35632 and AAA18355, respectively, and are incorporated herein by reference in their entirety. An addition source include zebrafish PDX nucleic acid and protein sequences are shown in GenBank Accession No. AF036325 and AAC41260, respectively, and are incorporated herein by reference in their entirety.

The compound can be administered to the subject either directly (i.e., the subject is directly exposed to the nucleic acid or nucleic acid-containing vector) or indirectly (i.e., cells are first transformed with the nucleic acid in vitro, then transplanted into the subject). For example, in one embodiment mammalian cells are isolated from a subject and the PDX nucleic acid introduced into the isolated cells in vitro. The cells are reintroduced into a suitable mammalian subject. Preferably, the cell is introduced into an autologous subject. The routes of administration of the compound can include e.g., parenteral, intravenous, intradermal, subcutaneous, oral (e.g., inhalation), transdermal (topical), transmucosal, and rectal administration. In one embodiment the compound is administered intravenous. Preferably, the compound is implanted under the kidney capsule or injected into the portal vein.

The cell can be any cell that is capable of producing pancreatic hormones, e.g., muscle, spleen, kidney, blood, skin, pancreas, or liver. In one embodiment the cell is capable of functioning as a pancreatic islet cell, i.e., store, process and secrete pancreatic hormones, preferably insulin upon an extracellular trigger. In another embodiment the cell is a hepatocyte, i.e., a liver cell. In additional embodiments the cell is tutipont or pluripotent. In alternative embodiments the cell is a hemopoietic stem cell, embryonic stem cell or preferably a hepatic stem cell.

The subject is preferably a mammal. The mammal can be, e.g., a human, non-human primate, mouse, rat, dog, cat, horse, or cow.

Methods of Inducing Pancreatic Hormone Production

In various aspects, the invention provides methods of inducing pancreatic hormone production in a subject. For example, the method can include administering to a subject a compound that increases PDX expression or activity in an amount sufficient to induce pancreatic hormone production.

In another aspect, the method includes providing a cell from a subject, contacting the cell with a compound which increases PDX expression in an amount sufficient to increase pancreatic hormone production and introducing the cell into a subject. In one embodiment pancreatic hormone production occurs in-vitro and in-vivo, upon introducing the cell into the subject. In an alternative embodiment, pancreatic hormone production occurs in-vivo upon introducing the cell in the subject.

The pancreatic hormone can be e.g., insulin, glucogon, somatostatin or islet amyloid polypeptide (IAPP). Insulin can be hepatic insulin or serum insulin. In another embodiment the pancreatic hormone is hepatic insulin. In an alternative embodiment the pancreatic hormone is serum insulin (i.e., a fully processed form of insulin capable of promoting, e.g., glucose utilization, carbohydrate, fat and protein metabolism).

In some embodiments the pancreatic hormone is in the "prohormone" form. In other embodiments the pancreatic hormone is in the fully processed biologically active form of the hormone. In other embodiments the pancreatic hormone is under regulatory control i.e., secretion of the hormone is under nutritional and hormonal control similar to endogenously produced pancreatic hormones. For example, in one aspect of the invention the hormone is under the regulatory control of glucose.

The cell population that is exposed to, i.e., contacted with, the compound can be any number of cells, i.e., one or more cells, and can be provided in vitro, in vivo, or ex vivo.

Methods of Treating or Preventing Pancreatic Related Disorders

Also included in the invention is a method of treating, i.e., preventing or delaying the onset of pancreatic related disorders in a subject. In various aspects the method includes administering to the subject a compound which modulates the PDX expression or activity. "Modulates" is meant to include increase or decrease PDX expression or activity. Preferably, modulation results in alteration of the expression or activity of PDX in a subject to a level similar or identical to a subject not suffering from the pancreatic disorder. In other aspects the method includes administering to the subject a compound which induces a non-pancreatic cell with pancreatic islet cell function, e.g., capable of expressing insulin, somatostatin or glucagon. In one embodiment the compound modulates PDX expression or activity.

The pancreatic disorder can be any disorder associated with the pancreas. For example, the method may be useful in treating pancreatic hormone insufficiencies, (e.g., diabetes), insulinomas, and hyperglycemia. Essentially, any disorder, which is etiologically linked to PDX activity, would be considered susceptible to treatment.

The herein-described PDX modulating compound when used therapeutically are referred to herein as "Therapeutics". Methods of administration of Therapeutics include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g. an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. Various delivery systems are known and can be used to administer a Therapeutic of the present invention including, e.g.: (i) encapsulation in liposomes, microparticles, microcapsules; (ii) recombinant cells capable of expressing the Therapeutic; (iii) receptor-mediated endocytosis (See, e.g., Wu and Wu, 1987. *J Biol Chem* 262:4429–4432); (iv) construction of a Therapeutic nucleic acid as part of a retroviral, adenoviral or other vector, and the like. In one embodiment of the present invention, the Therapeutic may be delivered in a vesicle, in particular a liposome. In a liposome, the protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,837,028; and U.S. Pat. No. 4,737,323, all of which are incorporated herein by reference. In yet another embodiment, the Therapeutic can be delivered in a controlled release system including, e.g.: a delivery pump (See, e.g., Saudek, et al., 1989. *New Engl J Med* 321:574 and a semi-permeable polymeric material (See, e.g., Howard, et al., 1989. *J Neurosurg* 71:105).

Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Bocca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (See, e.g., Joliot, et al., 1991. *Proc Natl Acad Sci USA* 88:1864–1868), and the like. Alternatively, a nucleic acid Therapeutic can be introduced intracellularly and incorporated within host cell DNA for expression, by homologous recombination or remain episomal.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of by the active ingredients that result in the therapeutic effect, whether administered in combination, serially or simultaneously.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. However, suitable dosage ranges for intravenous administration of the Therapeutics of the present invention are generally about 20–500 micrograms ($\mu$g) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient The duration of intravenous therapy using the Therapeutic of the present invention will vary, depending on the severity of the disease being treated and the condition and potential idiosyncratic response of each individual patient. It is contemplated that the duration of each in application of the protein of the present invention will be in the range of 12 to 24 hours of continuous intravenous administration. Ultimately the attending physician will decide on the appropriate duration of intravenous therapy using the pharmaceutical composition of the present invention.

Cells may also be cultured ex vivo in the presence of therapeutic agents or proteins of the present invention in order to proliferate or to produce a desired effect on or activity in such cells. Treated cells can then be introduced in vivo for therapeutic purposes.

Methods of Inducing Islet Cell Phenotype and Function

The invention also includes a method of inducing or enhancing a one or more pancreatic islet cell phenotypes in a cell. In one embodiment the pancreatic cell phenotype is induced in a non-islet cell type. The method includes contacting a cell with a compound that modulates islet cell specific transcription factors in an amount sufficient to induce or enhance the pancreatic islet cell phenotype, e.g., beta, alpha and delta islet cells. Preferably, the compound increases PDX expression, production or activity. Preferably the method induces a pancreatic islet β-cell phenotype.

By " pancreatic islet cell phenotype" is meant that the cell displaying one or more characteristics typical of pancreatic islet cell i.e. hormone production, processing, storage in secretory granules, nutritionally and hormonally regulated secretion or characteristic islet cell gene expression profile. The pancreatic islet cell phenotype can be determined for example by measuring pancreatic hormone production, e.g., insulin, somatostatin or glucagon. Hormone production can be determined by methods known in the art, e.g. immunoassay, western blot, receptor binding assays or functionally by the ability to ameliorate hyperglycemia implantation in a diabetic host.

The cell can be any cell that is capable of expressing a pancreatic islet cell phenotype, e.g., muscle, spleen, kidney, skin, pancreas, or liver. In one embodiment the cell is capable of functioning as a pancreatic islet cell, i.e., store, process and secrete pancreatic hormones, preferably insulin upon an extracellular trigger. In another embodiment the cell is a hepatocyte, i.e., a liver cell. In additional embodiments the cell is tutipont or pluripotent. In alternative embodiments the cell is a hematopoietic stem cell, embryonic stem cell or preferably a hepatic stem cell.

The cell population that is exposed to, i.e., contacted with, the compound can be any number of cells, i.e., one or more cells, and can be provided in vitro, in vivo, or ex vivo.

Methods of Inducing a Pancreatic Islet Gene Expression Profile

The invention also includes a method of inducing or enhancing a pancreatic islet gene expression profile in a subject or a cell. By "pancreatic gene expression profile" is meant to include one or more genes that are normally transcriptionally silent in non-endocrine tissues, e.g., PC1/3, insulin, glucagon or somatostatin. The method includes administering to a subject a compound that increases PDX expression or activity in an amount sufficient to induce a pancreatic islet or endocrine gene expression profile. In one embodiment the method induces PC1/3 gene expression in a subject.

Induction of the pancreatic gene expression profile can be detected using techniques well known to one of ordinary skill in the art. For example, pancreatic hormone RNA sequences can be detected in, e.g., northern blot hybridization analyses, amplification-based detection methods such as reverse-transcription based polymerase chain reaction or sytemic detection by microarray chip analysis. Alternatively, expression can be also measured at the protein level, i.e., by measuring the levels of polypeptides encoded by the gene. In a specific embodiment PC1/3 gene or protein expression can be determined by its activity in processing prohormones to their active mature form. Such methods are well known in the art and include, e.g., immunoassays based on antibodies to proteins encoded by the genes, or HPLC of the processed prohormones.

Methods of Identifying Genes the Expression of Which is Modulated by PDX

The invention also includes a method of identifying nucleic acids the expression of which is modulated by PDX. The method includes measuring the expression of one or more nucleic acids in a test cell population exposed to a compound that modulates PDX activity or expression. Expression of the nucleic acid sequences in the test cell population is then compared to the expression of the nucleic acid sequences in a reference cell population, which is a cell population that has not been exposed to the compound, or, in some embodiments, a cell population exposed the compound. Comparison can be performed on test and reference samples measured concurrently or at temporally distinct times. An example of the latter is the use of compiled expression information, e.g., a sequence database, which assembles information about expression levels of known sequences following administration of various agents, For example, alteration of expression levels following administration of compound can be compared to the expression changes observed in the nucleic acid sequences following administration of a control agent, such a PDX nucleic acid.

An alteration in expression of the nucleic acid sequence in the test cell population compared to the expression of the nucleic acid sequence in the reference cell population that has not been exposed to the compound indicates expression of the nucleic acid is modulated by PDX. The test cell can be taken from any tissue capable of being modulated by PDX, e.g., pancreas, liver, spleen, or kidney. In one embodiment the cell is from a non-endocrine tissue. Preferably, the cell is liver tissue.

Preferably, cells in the reference cell population are derived from a tissue type as similar as possible to test cell, e.g., liver tissue. In some embodiments, the control cell is derived from the same subject as the test cell, e.g., from a region proximal to the region of origin of the test cell. In other embodiments, the control cell population is derived from a database of molecular information derived from cells for which the assayed parameter or condition is known.

Expression of the nucleic acids can be measured at the RNA level using any method known in the art. For example, northern hybridization analysis using probes which specifically recognize one or more of these sequences can be used to determine gene expression. Alternatively, expression can be measured using reverse-transcription-based PCR assays. Expression can be also measured at the protein level, i.e., by measuring the levels of polypeptides encoded by the gene products. Such methods are well known in the art and include, e.g., immunoassays based on antibodies to proteins encoded by the genes.

When alterations in gene expression are associated with gene amplification or deletion, sequence comparisons in test and reference populations can be made by comparing relative amounts of the examined DNA sequences in the test and reference cell populations.

The invention also includes PDX modulated nucleic acids identified according to this screening method, and a pharmaceutical composition comprising the PDX modulated nucleic acids so identified.

PDX Recombinant Expression Vectors and Host Cells

Another aspect of the invention pertains to vectors, preferably expression vectors, containing a nucleic acid encoding a PDX protein, or derivatives, fragments, analogs or homologs thereof. As used herein, the term "vector" refers to a nucleic acid molecule capable of transporting another nucleic acid to which it has been linked. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PDX proteins, mutant forms of PDX, fusion proteins, etc.).

The recombinant expression vectors of the invention can be designed for expression of PDX in prokaryotic or eukaryotic cells. For example, PDX can be expressed in bacterial cells such as E. coli, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann el al., (1988) *Gene* 69:301–315) and pET 11d (Studier el al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the PDX expression vector is a yeast expression vector. Examples of vectors for expression in yeast *S. cerevisiae* include pYepSec1 (Baldari, et al., (1987) *EMBO J* 6:229–234), pMFa (Kujan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, PDX can be expressed in insect cells using baculovirus expression vectors. Baculovirus vectors available for expression of proteins in cultured insect cells (e.g., SF9 cells) include the pAc series (Smith et al. (1983) *Mol*

*Cell Biol* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufinan et al. (1987) *EMBO J* 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Baneiji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to PDX in mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub el al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Additionally, host cells could be modulated once expressing PDX, and may either maintain or loose original characteristics.

A host cell can be any prokaryotic or eukaryotic cell. For example, PDX protein can be expressed in bacterial cells such as *E. coli*, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector DNA can be introduced into prokaryotic or eukaryotic cells via conventional transformation, transduction, infection or transfection techniques. As used herein, the terms At "transformation" "transduction", "infection" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. In addition transfection can be mediated by a transfection agent. By "transfection agent" is meant to include any compound that mediates incorporation of DNA in the host cell, e.g., liposome. Suitable methods for transforming or transfecting host cells can be found in Sambrook, el al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

Transfection may be "stable" ( i.e. intergration of the foreign DNA into the host genome) or "transient" (i.e., DNA is episomally expressed in the host cells).

For stable transfection of mammalian cells, it is known that, depending upon the expression vector and transfection technique used, only a small fraction of cells may integrate the foreign DNA into their genome the remainder of the DNA remains episomal In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding PDX or can be introduced on a separate vector. Cells stably transfected with the introduced nucleic acid can be identified by drug selection (e.g., cells that have incorporated the selectable marker gene will survive, while the other cells die). In another embodiment the cells modulated by PDX or the transfected cells are identified by the induction of expression of a endogeneous reporter gene. In a specific embodiment, the promotor is the insulin promoter driving the expression of green flourescent protein (GFP).

In one embodiment the PDX nucleic acid is present in a viral vector. In another embodiment the PDX nucleic acid is encapsulated in a virus. In some embodiments the virus preferably infects pluripotent cells of various tissue type, e.g. hematopoietic stem, cells, neuronal stem cells, hepatic stem cells or embroyonic stem cells, preferably the virus is hepatropic. By "hepatotropic" it is meant that the virus has the capacity to preferably target the cells of the liver girt either specifically or non-specifically. In further embodiments the virus is a modulated hepatitis virus, SV40, or Epstein-Bar virus. In yet another embodiment, the virus is an adenovirus.

Gene Therapy

In one aspect of the invention a nucleic acid or nucleic acids encoding a PDX polypeptide, or functional derivatives thereof, are administered by way of gene therapy. Gene therapy refers to therapy that is performed by the administration of a specific nucleic acid to a subject. In this aspect of the invention, the nucleic acid produces its encoded peptide(s), which then serve to exert a therapeutic effect by modulating function of an aforementioned disease or disorder. e.g., diabetes. Any of the methodologies relating to gene therapy available within the art may be used in the practice of the present invention. See e.g., Goldspiel, et at., 1993. *Clin Pharm* 12:488–505.

In a preferred embodiment, the therapeutic comprises a nucleic acid that is part of an expression vector expressing any one or more of the aforementioned PDX polypeptides, or fragments, derivatives or analogs thereof, within a suitable host. In a specific embodiment, such a nucleic acid possesses a promoter that is operably-1inked to coding region(s) of a PDX polypeptide. The promoter may be inducible or constitutive, and, optionally, tissue-specific. The promoter may be, e.g., viral or mammalina in origin. In another specific embodiment, a nucleic acid molecule is used in which coding sequences (and any other desired sequences) are flanked by regions that promote homologous recombination at a desired site within the genome, thus providing for intra-chromosomal expression of nucleic acids. See e.g., Koller and Smithies, 1989. *Proc Natl Acad Sci USA* 86: 8932–8935. In yet another embodiment the nucleic acid that is delivered remains episomal and induces an endogenous and otherwise silent gene.

Delivery of the therapeutic nucleic acid into a patient may be either direct (i.e., the patient is directly exposed to the nucleic acid or nucleic acid-containing vector) or indirect (i.e., cells are first contacted with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, but not limited to, constructing said nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "Gene Gun®; Biolistic, DuPont); coating said nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. *J Biol Chem* 262: 4429–4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the methodology of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient.

In a specific embodiment, prior to the in vivo administration of the resulting recombinant cell, the nucleic acid is introduced into a cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth Enzymol* 217: 599–618. The chosen technique should provide for the stable transfer of the nucleic acid to the cell, such that the nucleic acid is expressible by the cell. Preferably, said transferred nucleic acid is heritable and expressible by the cell progeny. In an alternative embodiment, the transferred nucleic acid remains episomal and induces the expression of the otherwise silent endogenous nucleic acid.

In preferred embodiments of the present invention, the resulting recombinant cells may be delivered to a patient by various methods known within the art including, but not limited to, injection of epithelial cells (e.g., subcutaneously), application of recombinant skin cells as a skin graft onto the patient, and intravenous injection of recombinant blood cells (e.g., hematopoietic stem or progenitor cells) or liver cells. The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973–985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

Pharmaceutical Compositions

The compounds, e.g. PDX polypeptides, nucleic acid endowing PDX polypetides, or a nucleic acid that increases expression of a nucleic acid that encodes ad PDX polypeptide. (also referred to herein as "active compounds") of the invention, and derivatives, fragments, analogs and homologs thereof, can be incorporated into pharmaceutical compositions suitable for administration. Such compositions typically comprise the nucleic acid molecule, or protein, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PDX polypeptide or PDX encoding nucleic acid) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The nucleic acid molecules of the invention can be inserted into vectors and used as gene therapy vectors. Gene therapy vectors can be delivered to a subject by any of a number of routes, e.g., as described in U.S. Pat. No. 5,703,055. Delivery can thus also include, e.g., intravenous in injection, local administration (see U.S. Pat. No. 5,328,470) or stereotactic injection (see e.g., Chen el al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

The invention will be further described in the following examples, which do not limit the scope of the invention described in the claims.

SPECIFIC EXAMPLES

Example 1

Recombinant Adenoviruses

AdCMVPDX-1 was constructed as described in by R. Seijffers et al. *Endocrinology* 140:1 133(1999). It contains the STF-1 CDNA, the rat homolog of PDX-1 ligated into BamH1 site of pACCMVpLpA vector.

AdCMVβ-gal, contains the nuclear localization signal for β-galactosidase.

AdCMV-hIns, contains the human insulin CDNA under the control of the heterologous cytomegalovirus promoter.

AdRIP-1-hIns, contains the human insulin cDNA under the control of the rat insulin n promoter-1 (RIP-1). RIP-1, is 410 bases of the 5' flanking DNA region of the rat insulin-1 gene.

Example 2

Determination of PDX-1 Induced Endogenous Insulin Gene Expression and Activation of Ectopically Co-delivered Insulin Promoter To assess the effect of ectopic PDX-1 expression in the liver, male Balb/c and C57BL/6 mice (11–14 week old ) were injected with $2\times10^9$ plaque forming units (in 0.2 ml saline) of AdCMV-PDX-1 recombinant adenovirus into the tail vein. As controls, mice were similarity injected with AdCMV-β-gal, or AdCMV-hIns and AdRIP-1-hIns recombinant adenoviruses. The animals were housed in an air-conditioned environment, under a 12-hour light/dark cycle, on a regular unrestricted diet, and sacrificed one week following virus administration. The liver, spleen, pancreas and kidney were dissected and were immediately frozen in liquid nitrogen, and stored at −70° C. for total RNA isolation.

PDX-1 and insulin gene expression was determined by RT-PCR Total RNA was isolated from frozen tissues using RNAzol (CINNA-BIOTEX). RNA samples were treated by 10 ul of DNase I (Promega). CDNA was prepared by reverse transcription, using 1 μg DNA-free total RNA and 0.5 μg oligo(dT)$_{15}$ 1.5 μl of RT reaction was amplified using primers and PCR conditions as indicated in Table 1 below. PCR was carried out in a GeneAmp PCR system 2400 (Perkin Elmer), and products were separated on 1.7% agarose gel. A separate PCR reaction was carried out for each RNA sample without reverse transcriptase, to ensure that the amplified product was not due to DNA contamination. The primers were designed to detect the only the ectopic rat PDX-1 expression not the mouse homolog. The primers for mI-2 amplification are located on different exons. The first step of sample denaturation was identical for all amplified genes: 94° C. for 1 minute.

Analysis of the total RNA revealed that AdCMV-PDX-1 administration resulted in PDX-1 expression mainly in liver. Spleen, pancreas and kidney from the same mice tested negative by RT-PCR for the rat homolog of PDX-1.

75% (25 of 35) of the mice that tested positive for the ectopic rat PDX-1 message expressed the mI-2 gene whereas 35% of the mices expressed mI-1 gene (FIG. 1). To determine whether this disparity of expression between mI-2 and mI-1 was due the mI-1 promotor being differentially effected by the identity or the levels of transcription factors present in PDX-1 expressing liver cells, AdRIP-1-hIns recombinant adenovirus was co-delivered with AdCMV-PDX-1 to mice as described above. As demonstrated in FIG. 1, in livers where PDX-1 induced only the expression of the endogenous mI-2, it also activated the rate insulin-1 promoter (RIP-1). This suggests that the different levels of DNA methylation or distinct chromatin structure could be the cause of the low efficiency of the activation of the endogenous mI-1 expression by PDX-1 expression in the liver. Furthermore these data demonstrate the capacity to activate the β-cell specific insulin promotor in liver when co-delivered with PDX.

The expression of the endogenous mouse insulin and the ectopic human insulin genes was not induced by treatment with the same concentration of the control recombinant adenoviruses AdCMV-β-gal, or AdCMV-hIns and AdRIP-1hIns, respectively (n=20). These results demonstrate that PDX-1 is essential and sufficient to induce expression of the endogenous insulin genes and to activate RIP-1 in an extra-pancreatic tissue.

Example 3

Determination of PDX-1 Induced Somatostatin Gene Expression and Protein Production In-vivo Animals were treated with recombinant adenovirus as described in EXAMPLE 2. Somatostatin gene expression was determined by RT-PCR as described in EXAMPLE 2, according to the conditions described in Table 1.

Figure 3:
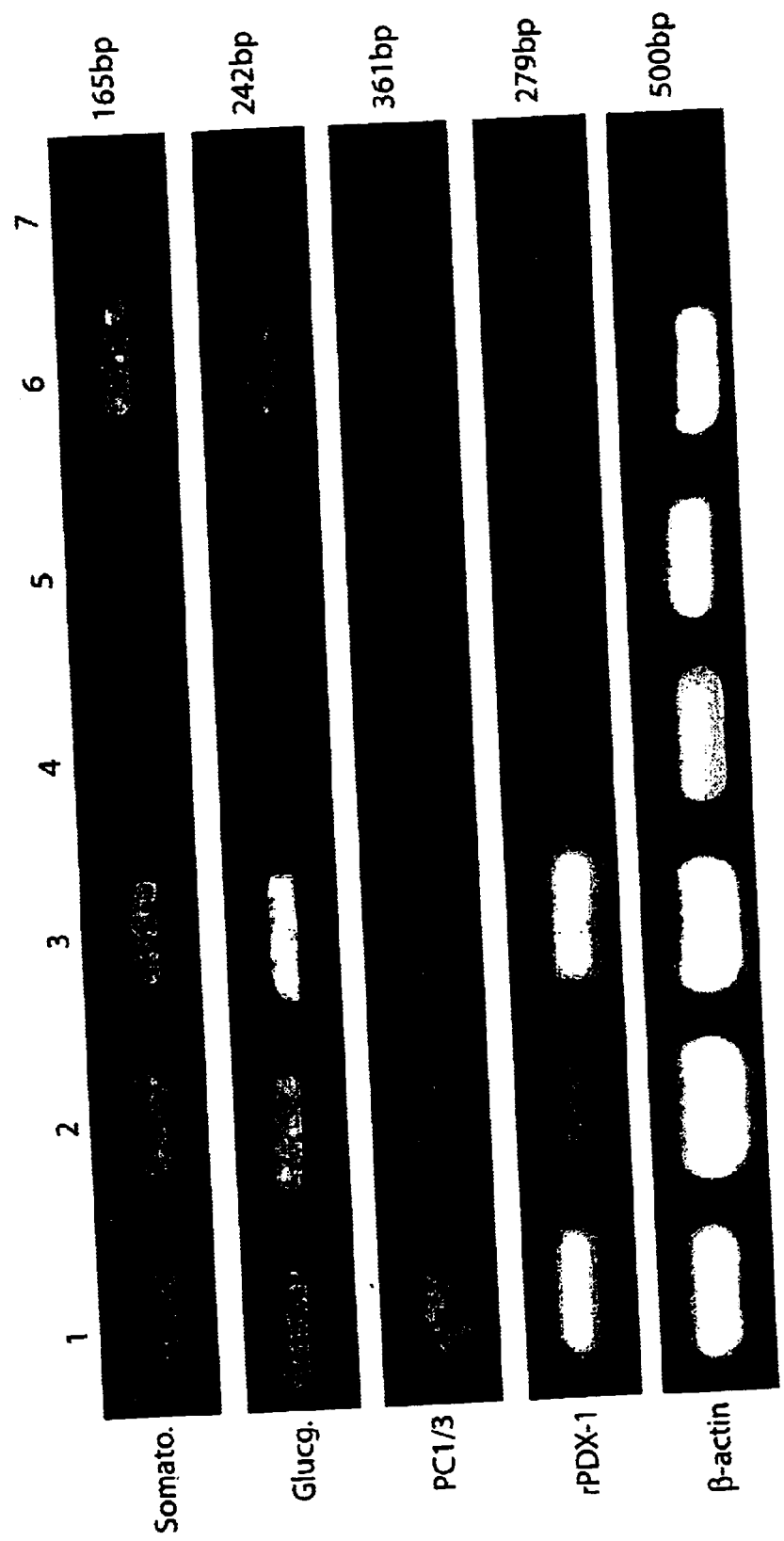
FIG. 3 is an illustration demonstrating detection of mRNA for PDX-1, somatostatin in Somato), proinsulin convertase PC1/3 (PC1/3), glucagon (Glucg) and β-actin determined by RT-PCR: Total RNA extracted from PDX-1 and control treated mice was reverse-transcribed using a PC1/3 specific primer lanes 1–3: mice treated by AdCMV-PDX-1; lanes 4–5: mice treated by AdCMV-β-gal; lane 6: pancreas; lane 7: no cDNA, (control for PCR).

As demonstrated in FIG. 3 livers in mice treated with AdCMV-PDX-1 exhibited somatostatin gene expression. Mice treated with AdCMV-PDX-1 exhibited positive staining for the somatostatin prolin in liver tissue analyzed by inmmunochemistry. Mice treated with AdCMV-β-gal did not express somatostatin.

Example 4

Determination of PDX-1 Induced Glucagon Gene Expression

Animals were treated with AdCMVPDX-1 recombinant adenovirus as described in EXAMPLE 2 Glucagon gene expression was determined by RT-PCR as described in EXAMPLE 2, using conditions and primers as described in Table 1.

As demonstrated in FIG. 3 livers in mice treated with AdCMV-PDX-1 exhibited glucagon gene expression. Mice treated with AdCAdV-β-gal did not express glucagon.

Example 5

Determination of Prohormone Convertase 1/3 Induced Gene Expression

Animals were treated with recombinant adenovirus as described in EXAMPLE 2. Prohormone convertase 1/3

(PC1/3) gene expression was determined by RT-PCR as described in EXAMPLE 2 with the exception that cDNA was reverse-transcribed using a gene specific oligonucleotide (TCCAGGTGCCTACAG GATTCTCT) (SEQ ID NO: 1) instead of oligo (dT)$_{15}$). As demonstrated in FIG. 3 only livers from animals treated with PDX-1 exhibited the induction of PC1/3 expression, a member of the Kexin family proteases, PC1/3 expression is restricted to endocrine and neuroendocrine cells with regulated secretory pathway. Taken together with the capacity to retain the produced hormones in intracellular compartments suggests a PDX-1 dependent induction of an endocrine phenotype which includes the induction of a regulated pathway for hormone production, processing, storage and secretion.

Slides were exposed to the secondary biotinylated IgG for 30 minutes, incubated in streptavidin-peroxidase followed by chromogen-peroxide solution.

Immunohistochemical analysis of liver sections from mice treated with PDX-1, revealed expression of the homeoprotein in 30–60% of hepatocyte nuclei, with 0.1–1% of the liver cells staining positive for (pro)insulin. Control AdCMVβ-gal treated livers, did not stain positive for (pro) insulin although β-galactosidase activity was evident in 50% of the nuclei. Livers from mice treated by AdCMV-hIns, did not stain positive for insulin in the hepatic sections, although serum IRI from the same mice was three fold increased, as were serum IRI levels in PDX-1 treated mice. The fact that the ectopic expression of PDX-1 but not of insulin resulted

TABLE 1

RT-PCR analysis for determination of PDX-1 induced gene-expression.

| Gene | Primer Sequences 5'-3' | PCR Product | Annealing °C. | Annealing sec | Extention °C. | Extention sec | Cycles |
|---|---|---|---|---|---|---|---|
| Rat PDX-1 (ectopic) | F: CCAGTTTGCAGGCTCGCTGG (SEQ ID NO: 2) R: GCTGCGTATGCACCTCCTGC (SEQ ID NO: 3) | 279 bp | 62 | 60 | 72 | 60 | 31 |
| Human Insulin (ectopic) | F: CTTTGTGAACCAACACCTGTGC (SEQ ID NO: 4) R: GCAGATGCTGGTACAGCATTGT (SEQ ID NO: 5) | 239 bp | 63 | 60 | 72 | 60 | 38 |
| Mouse Insulin I | F: TTGCCCTCTGGGAGCCCAAA (SEQ ID NO: 6) R: CAGATGCTGGTGCAGCACTG (SEQ ID NO: 7) | 253 bp | 62 | 60 | 72 | 60 | 38 |
| Mouse Insulin II | F: TCTTCCTCTGGGAGTCCCAC (SEQ ID NO: 8) R: CAGATGCTGGTGCAGCACTG (SEQ ID NO: 9) | 259 bp | 62 | 60 | 72 | 60 | 38 |
| Mouse-actin | F: ATGGATGACGATATCGCT (SEQ ID NO: 10) R: ATGAGGTAGTCTGTCAGGT (SEQ ID NO: 11) | 500 bp | 56 | 45 | 72 | 60 | 35 |
| Mouse PC1/3 | F: CTGGTTGTCTGGACCTCTGAGTA (SEQ ID NO: 12) R: CCAACAGCAGAAGTGAGTGTGAC (SEQ ID NO: 13) | 361 bp | 55 | 45 | 72 | 60 | 38 |
| Mouse PDX-1 (endogenous) | F: CAAGCTCGCTGGGATCACTGGAGCAG (SEQ ID NO: 14) R: GATGTGTCTCTCGGTCAAGTTCAACATC (SEQ ID NO: 15) | 421 bp | 58 | 45 | 72 | 60 | 38 |
| Mouse & Rat somatostatin | F: CCTGGCTTTGGGCGGTGTCA (SEQ ID NO: 16) R: CTCGGGCTCCAGGGCATCATTC (SEQ ID NO: 17) | 165 bp | 68 | 45 | 72 | 60 | 38 |
| Mouse glucagon | F: ACCAGCGACTACAGCAAATACCTC (SEQ ID NO: 18) R: AGCAATGGCGACTTCTTCTGG (SEQ ID NO: 19) | 242 bp | 60 | 45 | 72 | 60 | 38 |
| rat insulin-1 | F: GTGACCAGCTACAATCATAG (SEQ ID NO: 20) R: AGTTCTCCAGTTGGTAGAGG (SEQ ID NO: 21) | 370 bp | 57 | 45 | 72 | 60 | 38 |
| Rat-actin | F: CGTAAAGACCTCTATGCCAA (SEQ ID NO: 22) R: AGCCATGCCAAATGTGTCAT (SEQ ID NO: 23) | 350 bp | 57 | 45 | 72 | 60 | 35 |

Example 6

PDX-1 Induced Proinsulin Synthesis in Livers

Animals were treated with recombinant adenovirus as described in EXAMPLE 2. Liver, spleen, pancreas and kidney were dissected. Portions of the tissue fixed in 4% formaldehyde and embedded in paraffin for immunohistochemical staining. The remaining liver and pancreatic tissues were homogenized in 70% ethanol-0.18N HCl, lyophilized and resuspended in PBS (phosphate buffered saline) for RIA determination of IRI content.

Immunohistochemisty

Five μm sections of paraffin-embedded tissues were deparaffinized, incubated in 3% $H_2O_2$, and then, either microwaved in citrate buffer for antigen retrieval prior to incubation in blocking solution (PDX-1 detection), or immediately exposed to the blocking solution (insulin detection). (Histomouse™-SP Kit, Zymed laboratories, Calif., USA).

PDX-1 detection: sections were incubated overnight at 4° C. with antiserum raised against the N-terminal portion of frog PDX-1.

Insulin detection: sections were incubated for 1 hour at 37° C. with a monoclonal anti-human-insulin (Sigma, St.-Louis Mo.).

in positive immunostaining for (pro)insulin may suggest the induction of a cellular modulation which supports insulin retention in a small subpopulation of liver cells, (secretory vesicles which belong to the regulated pathway, characteristic to endocrine cells, but not to liver cells), which may have shifted toward a β-cell phenotype.

Radioimmunoassay

To determine whether hepatic insulin mRNA is effectively translated into protein, immunoreactive insulin (IRI) content was tested in extracts derived from hepatic tissue by radioimmunoassay (RIA). Livers from PDX-1 treated mice that tested positive for insulin gene expression by RT-PCR (FIG. 1) contained about 25 fold more IRI than livers of animals treated by a control virus (Table 2). Mean IRI levels in extracts derived from PDX-1 treated livers was 20.7±3.97 μU/mg protein, while in control livers, IRI was only 0.78±0.25 μU/mg protein. The background level of insulin measured in control liver samples possibly represents insulin (of pancreatic origin) bound to its receptors which are abundant in this organ. While IRI detected in PDX-1 treated liver extracts was <1% of the levels detected in pancreatic extracts (Table 2), serum IRI levels in PDX-1 treated mice were almost 3-fold higher compared to controls (323±48.4 vs. 118.2±23.7 μU/ml, respectively (Table 2)), indicating that insulin was being synthesized and a large portion of it secreted into the blood stream. These data indicate that the insulin gene expression induced by the molecular manipulation is successfully translated into specific hepatic production of the pro/hormone.

Immunoreactive insulin detected in PDX-1 treated livers was less than 1% of IRI levels in pancreatic extracts (Table 2). The IRI values determined by radioimmunoassay (RIA) in liver extracts may under-estimate the actual insulin production in this organ. The antibody we used for RIA preferentially binds the processed hormone, and has only 60% cross-reactivity with proinsulin, which is expected to be present mainly in hepatocytes and to a much lower extent in pancreas.

Example 7

Blood Glucose and Serum Insulin Levels

Animals were treated with recombinant adenovirus as described in EXAMPLE 2. Prior to sacrifice, blood was drawn from the inferior vena cava for determination of glucose concentration (Accutrend® GC, Boehringer Mannheim, Mannheim, Germany) and insulin levels by radioimmunoassay (Coat-a-count, DPC, Los-Angeles, Calif., USA, using rat insulin standards, (Linco), the anti-insulin antibody used has only 60% cross-reactivity with human proinsulin).

Mice treated by AdCMV-PDX-1 recombinant adenoviruses were not hypoglycemic, however, their blood glucose levels were significantly lower than of mice treated by AdCMV-β-gal or AdCMV-Luc [197±11.2 vs. 228±15.74 mg/dl, respectively (Table 2). Plasma immunoreactive insulin levels were significantly higher in PDX-1 treated mice compared to controls (323±48.4 vs. 118.2±23.7 μU/ml respectively (Table 2).

The three fold increase in serum IRI levels in PDX-1 treated mice, cannot by itself explain the twenty-fivefold increase (Table 2) in hepatic IRI content demonstrated in PDX-1 treated liver extracts. Thus, the increase in hepatic pro/insulin content originates from local production.

TABLE 2

Blood glucose and immunoreactive insulin (IRI) levels in serum and liver extracts.

| | Control virus treated mice | AdCMV-PDX-1 treated mice |
|---|---|---|
| Blood glucose, mg/dl | 228 ± 15.74 (n = 18) | 197 ± 11.2 (n = 40) |
| Serum IRI, μU/ml | 118.2 ± 23.7 (n = 14) | 323 ± 48.4 (n = 26) |
| Liver extracts IRI μU/mg protein | 0.78 ± 0.25 (n = 10) | 20.7 ± 3.97 (n = 12) |
| Pancreas extracts IRI μU/mg protein | 2627 ± 24 (n = 6) | |

Example 8

HPLC Analysis of Insulin-related Peptides

Animals were treated with recombinant adenovirus as described in EXAMPLE 2. Liver, and pancreas were dissected and homogenized in 70% ethanol-0.18N HCl, lyophilized and resuspended in 0.1 M HCl—0.1% BSA for HPLC analysis.

Insulin-related peptides from the liver and pancreatic extracts were resolved by reverse-phase HPLC using Lichrospher 100 RP-18 column (Merck, Darmstadt, Germany) and elution conditions as described by Gross et al. One ma fractions were collected into tubes containing 0.1 ml 0.1% BSA in water, dried in a Speed-Vac apparatus and reconstituted in 1 ml RIA buffer (0.1% BSA in PBS) for peptide determination by RIA. Guinea pig antiporcine insulin antibodies (Linco, St Charles, Mo.) with either rat or human insulin standards were used for determination of mouse or human IRI, respectively.

Figure 2A:
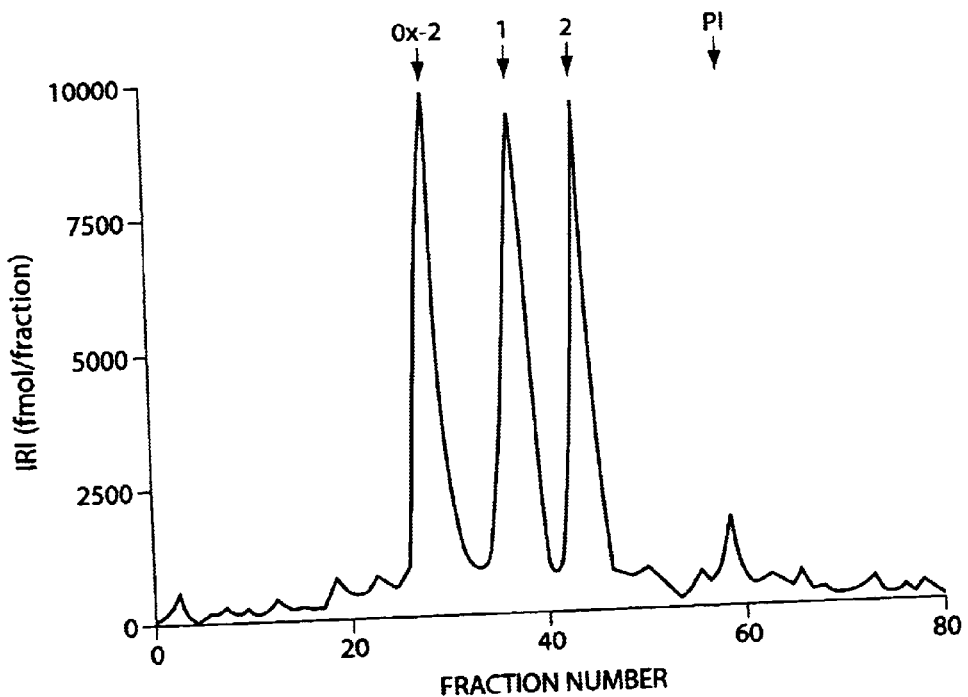
FIG. 2 is an illustration of the HPLC elution profiles of insulin related peptides extracted from murine tissue. Panel A shows the profile from the pancreas of a PDX-1 treated mouse. Panel B shows the profile from the liver of a PDX-1 treated mouse.
Figure 2B:
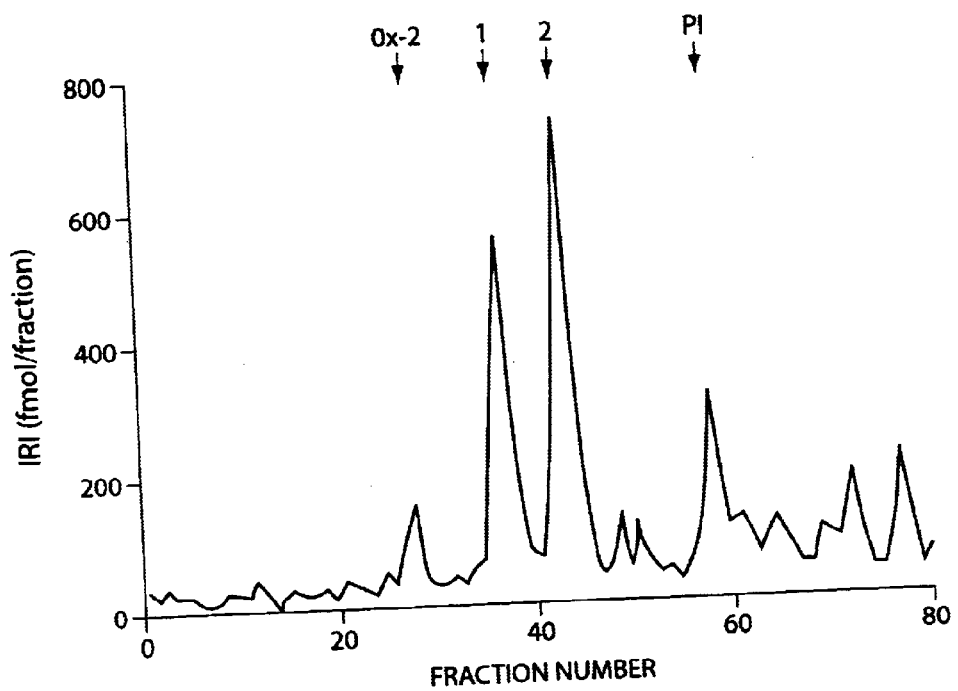

HPLC analysis of hepatic IRI content from PDX-1 treated mice revealed 59±7% (n=3) conversion into filly processed mI-1 and mI-2. In comparison, pancreatic extracts contained 85±5% (n=3) mature insulin (FIG. 2) Whereas, ectopic expression of human insulin (AdCMV-hIns) did not result in retention of IRI in the liver cells except for one liver in which most of the extracted IRI was immature insulin. This is in line with previous observations in transfected FAO cells in which no retention of the insulin gene product observed and most of it was secreted by the constitutive secretory pathway. These data demonstrates that ectopic PDX-1 expression in liver induces a cellular machinary, characteristic to endocrine tissue capable of processing the induced prohormone, and is not induced when only proinsulin is ectopically expressed in liver. Thus, inducing an extended β-cell phenotype in liver cells by ectopic PDX-1 expression.

Example 9

Biological Activity of Hepatic Pro/insulin Production

Figure 4:
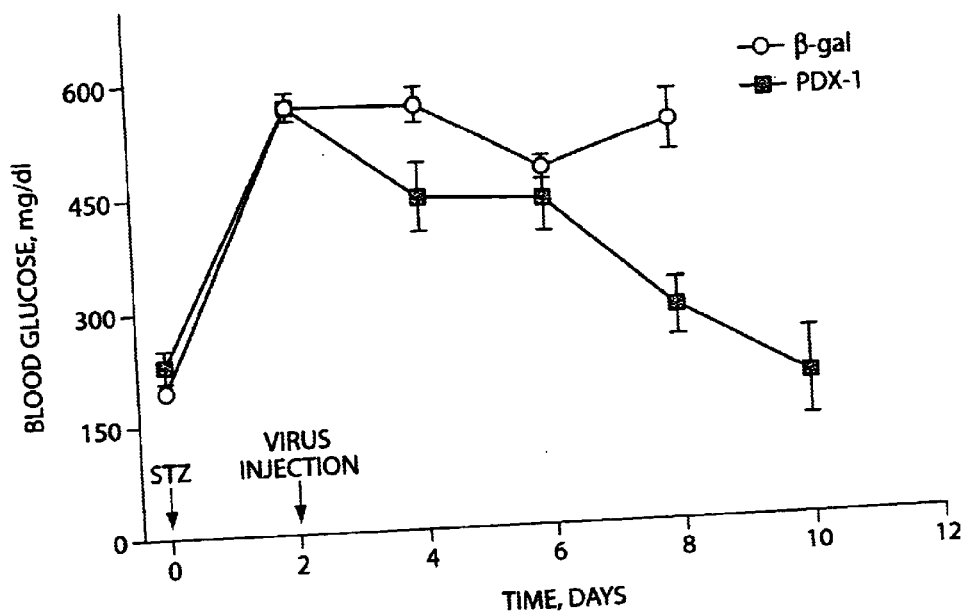
FIG. 4 is an illustration demonstrating ectopic PDX-1 expression in mice livers ameliorates STZ induced hyperglycemia: C57BL/6 males at 12–13 weeks were treated by 220 mg/kg STZ in citrate-buffer. 36–48 hour after STZ treatment mice were injected by AdCMVPDX-1 (n=15 mice), or as control by AdCMVβ-gal (n=22, however, 12 died 3–5 days after STZ treatment, additional 3 mice died 6–7 days after STZ treatment). No mortality occurred upon AdCMVPDX-1 treatment. Each treatment included systemic injection of $2\times10^9$ PFU (plaque forming units) of recombinant adenovirus in 200 µl saline. Glucose levels were determined in blood samples drawn from the ocular vein.

The ability of PDX-1-induced hepatic insulin production to control blood glucose levels in diabetic mice was studied. C57BL/6 mice were rendered diabetic (>600 mg/dl) with ketoacidosis, 24 hours after 200 mg/kg intraperitoneal STZ injection. 24–48 hours after STZ injection, mice were treated by either AdCMV-PDX-1 or by AdCMVβ-gal (control) recombinant adenoviruses administered via the tail vein, in saline solution. As demonstrated in FIG. 4, AdCMV-PDX-1 treated mice, exhibited gradual decrase in blood glucose levels from about 600 to 200–300 mg/dl starting two days after recombinant adenoviral treatment In contrast, in the control AdCMVβ-gal treated mice, hyperglycemia persisted and was accompanied by increased rate of mortality, 12 out of 22 tested died, with severe ketoacidosis 1–3 days after adenovirus treatment. Furthermore, both groups lost weight after induction of hyperglycemia, and did not regain it back before mice were sacrificed. In summary, the data demonstrate that expression of PDX-1 is sufficient to induce mature, biologically active insulin production in liver which ameliorates hyperglycemia in mice bearing ablated 0cell function.

Example 10

In-vitro Activation of Insulin Promoter by Ectopic PDX-1 Expression

PDX-1 activates rat insulin-1 promotor when co-delivered with a recombinant adenovirus AdRip-1hIns in which human insulin expression is delivered by a rat insulin-1 promoter. (See, EXAMPLE 2 and FIG. 1. PDX-1 was shown to be sufficient to activate rat insulin promoter-1 in-vitro in rat liver cells. Primary cultures if mature and fetal hepatocytes were cultured on collagen-1 covered tissue culture dishes in serum free chemically defined media. Two days after to plating cells were treated by either AdCMV-PDX-1 & AdRIP-1hIns or by AdCMV β-gal & AdRIP-1hIns. 48 hours after adenoviral treatment, total RNA was extracted and proinsulin genes expression was assessed as described in EXAMPLE 2.

Figure 5:
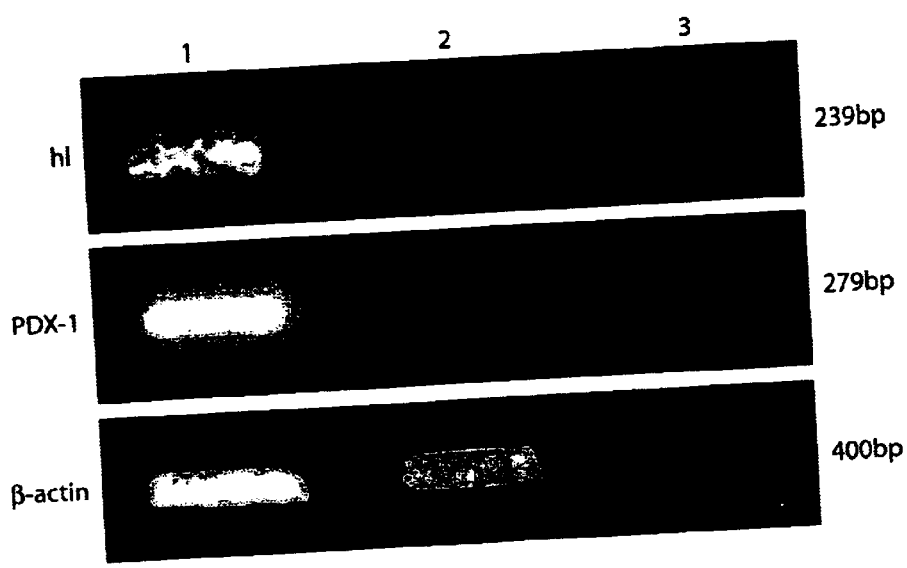
FIG. 5 is an illustration demonstrating ectopic PDX expression in mature hepatocytes in culture activates insulin promoter (rat insulin-1 promoter), co-delivered to the same cells by AdRIPhIns. Human insulin is detected as in FIG. 1.

PDX-1 activated the ectopically expressed RIP-hIns (rat insulin promoter-1, 410 bps of this promoter, driving human insulin, introduced via recombinant adenovirus), while β-gal did not possess such a capacity. (FIG. 5)

Example 11

In-vitro Induction of Endogenous Somatostatin Gene Expression in Hepatocytes

Primary cultures of hepatocytes isolated from fetal (E14-Fisher-344 rats) were cultured and treated by recombinant adenoviruses as described in EXAMPLE 9. Somatostatin gene expression was detected in reverse transcribed total RNA samples as described in EXAMPLE 2, using primers and RT-PCR conditions as described in Table 1.

The data demonstrate that ectopic PDX-1 expression in hepatocytes in-vitro induces the expression of the endogenous, otherwise silent somatostatin gene expression in hepatocytes, in-vitro (FIG. 6).

Example 12

In-vitro Induction of Endogenous Insulin Gene Expression in Hepatocytes

Primary cultures of fetal (E14-Fisher-344 rats) were cultured and treated by recombinant adenoviruses as described in EXAMPLE 10. Rat insulin 1 gene expression was detected in reverse transcribed total RNA samples as described in EXAMPLE 2, using primers and RT-PCR conditions as described in Table 1.

The data demonstrate that ectopic PDX-1 expression in primary culture of fetal hepatocytes in-vitro induces the expression of the endogenous, otherwise silent insulin gene expression (FIG. 6).

Example 13

Ectopic PDX-1 Expression in Liver Cells Induces an Intracellular Compartment Characteristic of Endocrine and Neuroendocrine Cells Which Allows the Retention of the Produced Hormones, and its Regulated Secretion Mice were treated with either Ad-CMVhIns or AdCMVPDX-1 as described in EXAMPLE 2. Treatment resulted in a three-fold increase serum IRI demonstrating human insulin production by liver cells (FIG. 1). Cells positive for the insulin protein by immnunocytochemistry were detected only in AdCMVPDX-treatment. Moreover, HPLC analysis of liver extracts detected only trace levels of IRI in liver extracts all of it unprocessed in the Ad-CMVhIns treated mice compared to 25 fold increase in the AdCMVPDX-1 treated mice. Furthermore, 59% of the insulin produced in AdCMVPDX-1 treated mice was processed. In addition, only livers treated by AdCMVPDX-1 exhibited the induction of the prohormone processing enzyme PC1/3 which is characteristic only to cells capable of regulated pathway for insulin processing storage and regulated secretion. These data demonstrate that PDX induces the regulated secretion of insulin in liver cells Example 14

Identification of Nucleic Acids the Expression of Which is Modulated by PDX

Nucleic acids modulated by PDX are identified by ectopic PDX expression. Nucleic acids that are not expressed in control treated extra-pancreatic islet tissue, as compared to pancreatic tissue are the nucleic acids modulated by PDX. These nucleic acids so identified are used as therapeutic compounds to treat pancreatic associated disorders.

Identification of the target genes is performed by either subtractive libraries, commercially available microarray Chips (Incyte, or Affimetrix), or membrane hybridizations (CLONTECH. Atlas™ expression arrays, or Multiple Tissue Northern (MTN) Blots). RNA isolation from treated tissues, its purification, and cDNA probe synthesis is performed according to manufacturer instructions.

The genes which are expressed in the PDX treated non-pancreatic islet tissue and are also present in pancreatic islets probed membranes or chips, but not in control treated non-pancreatic islet tissue, are the direct and non-direct PDX target genes, which represent the islet cells characteristic profile of gene expression. Discrimination between direct or indirect is elucidated by candidate target gene promoter analysis by electromobility shift assay (EMSA) as in FIG. 7, At and promoter footprinting (as described in Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Example 15

Inducing Regulated Expression of a Desired Ectopically Expressed Gene in Host Tissue This EXAMPLE illustrates the induction of regulated expression of any reporter, in addition to insulin. When PDX activates the insulin promoter in non pancreatic islet tissue, and mediates its glucose and growth factors sensing ability, than, any additional promotor will be similarly regulated by glucose and growth factors. Thus, this invention can be utilized to nutritionally and hormonally regulate expression of numerous secreted/or non secreted factors such as for example, glucagon, growth hormone, steroid hormones which are driven by the insulin promoter thus controlling their transcription, and regulated secretion, from an otherwise non-endocrine tissue. (FIG. 7.)

Example 16

Identification of PDX Location in the Hierarchy of B or Islet Cell Specific Transcription Factors This EXAMPLE illustrates the identification of the PDX location in the hierarchy of β-cell or islet cell specific transcription factors. Every transcription factor expressed in pancreatic islets but is not induced by ectopic PDX-1 expression in liver, could cooperate with PDX for the induction of a more comprehensive, complete or close to complete β-cell phenotype in non-endocrine-pancreatic tissue, such as liver. The detection of induced expression of islet cell specific transcription factors in liver is performed as in EXAMPLE 2, using the appropriate primers and conditions the example of which is elaborated in Table 1.

An additional method to analyze the activity of transcription factors is performed by footprinting, and by ElectroMobility Shift Assays (EMSA): Nuclear extracts (3–4 μg of protein) were incubated on ice for 10 minutes in DNA binding mixture containing 10% Glycerol, 15 mM Hepes (pH 7.9), 150 mM KCl, 5 mM DTT and 0.3 μg of poly dIdC, poly dAdT (SIGMA St-Louis Mo.). After the first incubation, approximately 0.2 ng of the probe was added for an additional 25 minutes incubation on ice, The binding reaction was analyzed on a native 4% polyacrylamide gel.

Oligonucleolides (probes). Synthetic double-stranded oligonucleotides are end-labeled with [a32P]ATP using the Klenow fragment of DNA polymerase. The sequences of oligonucleotides A3/A4 which is an example for PDX-1 binding site (one of them) on the insulin promoter 5'GATCT-GCC CCTTGTTAATAATCTAATG 3'(SEQ ID NO: 24). The sequence for A1 (additional PDX-1 binding site on insulin promoter) is 5' GATCCGCCCTTAATGGGCCAAACGGCA-3' (SEQ ID NO: 25). The labeled oligos are used as probes for electromobility shift assays, as described in FIG. 7. The identity of PDX-1 is double estimated by supershift using a specific antibody which prevents the PDX-1 binding to its cognate locus on the promoter, or that increases the molecular weight of the complex separated on PAGE (antibody+pdx-1+probe) compared to that which includes only pdx-1+labeled probe (last two lanes in FIG. 7).

Equivalents

From the foregoing detailed description of the specific embodiments of the invention, it should be apparent that unique methods of inducing pancreatic hormone production has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. A method of inducing pancreatic hormone expression in the liver of a mammal, wherein said pancreatic hormone is selected from the group consisting of insulin, somatostatin, and glucagon, said method comprising administering to a mammal an adenoviral particle comprising an adenovirus vector comprising a cytomegalovirus (CMV) promoter operably linked to a nucleic acid encoding a pancreatic and duodenal homobox 1 (PDX-1) polypeptide in an amount sufficient to induce said pancreatic hormone expression in said liver in said mammal.

2. The method of claim 1, wherein administering said vector increases hepatic insulin levels in said mammal.

3. The method of claim 1, wherein administering said vector increases serum insulin levels in said mammal.

4. The method of claim 1, wherein the mammal is a rodent or human.

5. The method of claim 1, wherein the mammal is further administered a transfection agent.

6. The method of claim 1, wherein the administering is by intravenous delivery.

7. A method of inducing a pancreatic islet gene expression profile in a liver cell of a subject, said method comprising administering to a subject an adenoviral particle comprising an adenovirus vector comprising a cytomegalovirus (CMV) promoter operably linked to a nucleic acid encoding a pancreatic and duodenal homobox 1 (PDX-1) polypeptide in an amount sufficient to induce said pancreatic islet gene expression in said liver cell in said subject.

8. A method of inducing insulin expression in the liver of a mammal, said method comprising administering to a mammal an adenoviral particle comprising an adenovirus vector comprising a cytomegaloviras (CMV) promoter operably linked to a nucleic acid encoding a pancreatic and duodenal homobox 1 (PDX-1) polypeptide in an amount sufficient to induce said insulin expression in said liver of said mammal.

9. A method of inducing glucagon expression in the liver of a mammal, said method comprising administering to a mammal an adenoviral particle comprising an adenovirus vector comprising a cytomegalovirus (CMV) promoter operably linked to a nucleic acid encoding a pancreatic and duodenal homobox 1 (PDX-1) polypeptide in an amount sufficient to induce said glucagon expression in said liver of said mammal.

10. A method of inducing somatostatin expression in the liver of a mammal, said method comprising administering to a mammal an adenoviral particle comprising an adenovirus vector comprising a cytomegalovirus (CMV) promoter operably linked to a nucleic acid encoding a pancreatic and duodenal homobox 1 (PDX-1) polypeptide in an amount sufficient to induce said somatostatin expression in said liver of said mammal.

11. A method of inducing prohormone convertase 1/3 (PC1/3) expression in the liver of a mammal, said method comprising administering to a mammal an adenoviral particle comprising an adenovirus vector comprising a cytomegalovirus (CMV) promoter operably linked to a nucleic acid encoding a pancreatic and duodenal homobox 1 (PDX-1) polypeptide in an amount sufficient to induce said PC1/3 expression in said liver of said mammal.

12. A method of inducing pancreatic hormone expression in a liver cell, wherein said pancreatic hormone is selected from the group consisting of insulin, somatostatin, and glucagon, said method comprising contacting said cell with an adenovirus vector comprising a cytomegalovirus (CMV) promoter operably linked to a nucleic acid encoding a pancreatic and duodenal homobox 1 (PDX-1) polypeptide, thereby inducing said pancreatic hormone expression in said liver cell.

13. A method of inducing insulin expression in a liver cell, said method comprising contacting said cell with an adenovirus vector comprising a cytomegalovirus (CMV) promoter operably linked to a nucleic acid encoding a pancreatic and duodenal homobox 1 (PDX-1) polypeptide, thereby inducing said insulin expression in said liver cell.

14. A method of inducing somatostatin expression in a liver cell, said method comprising contacting said cell with an adenovirus vector comprising a cytomegalovirus (CMV) promoter operably linked to a nucleic acid encoding a pancreatic and duodenal homobox 1 (PDX-1) polypeptide, thereby inducing said somatostatin expression in said liver cell.

15. A method of inducing glucagon expression in a liver cell, said method comprising contacting said cell with an adenovirus vector comprising a cytomegalovirus (CMV) promoter operably linked to a nucleic acid encoding a pancreatic and duodenal homobox 1 (PDX-1) polypeptide, thereby inducing said glucagon expression in said liver cell.

16. A method of inducing prohormone convertase 1/3 (PC1/3) expression in a liver cell, said method comprising contacting said cell with an adenovirus vector comprising a cytomegalovirus (CMV) promoter operably linked to a nucleic acid encoding a pancreatic and duodenal homobox 1 (PDX-1) polypeptide, thereby inducing said PC1/3 expression in said liver cell.

17. A composition comprising an adenovirus vector comprising a cytomegalovirus (CMV) promoter operably linked to a nucleic acid encoding a pancreatic and duodenal homobox 1 (PDX-1) polypeptide, and a carrier.

* * * * *